United States Patent [19]

Haigwood et al.

[11] Patent Number: 5,501,853
[45] Date of Patent: Mar. 26, 1996

[54] PEPTIDE PLASMINOGEN ACTIVATORS

[75] Inventors: Nancy L. Haigwood, Oakland, Calif.; Ernest-Guenter Afting, Marburg, Germany; Guy Mullenbach, Oakland, Calif.; Eric P. Paques, Marburg, Germany

[73] Assignees: Chiron Corporation, Emeryville, Calif.; Behringwerke AG, Marburg, Germany

[21] Appl. No.: 944,117

[22] Filed: Dec. 22, 1986

Related U.S. Application Data

[63] Continuation-in-part of Ser. No. 812,879, Dec. 3, 1985, abandoned.

[51] Int. Cl.[6] .............................. C12N 15/00; C12N 9/64; A61K 38/49
[52] U.S. Cl. ................ 424/94.64; 435/226; 435/69.1; 424/94.63
[58] Field of Search .................................. 435/212, 215, 435/226.91, 172.3, 240.2, 253, 320, 219, 226, 69.1, 320.1, 240.2; 424/10, 14, 27, 29, 32, 50, 70, 71, 73, 16, 94.63, 94.64; 536/27, 23.2

[56] References Cited

U.S. PATENT DOCUMENTS

| | | |
|---|---|---|
| 4,751,084 | 6/1988 | Feder et al. . |
| 4,753,879 | 6/1988 | Rosa et al. . |
| 5,073,494 | 12/1991 | Heyneker et al. ................. 435/226 |
| 5,106,741 | 4/1992 | Marotti et al. ..................... 435/226 |
| 5,147,643 | 9/1992 | Heyneker et al. ................. 424/94.64 |
| 5,344,773 | 9/1994 | Wei et al. ........................... 435/226 |

FOREIGN PATENT DOCUMENTS

8401786  5/1984  WIPO ................................ 435/212

OTHER PUBLICATIONS

Gordon A. Vehar et al., "Characterization Studies on Human Melanoma Cell Tissue Plasminogen Activator," Biotechnology, vol. 2, pp. 1051–1057 (1986).
Diane Pennica et al., "Cloning and Expression of Human Tissue-Type Plasminogen Activator cDNA in *E. coli.*", Nature, vol. 301, No. 5897, pp. 214–221.
Pohl, G. et al, Biochemistry, vol. 23, pp. 3701–3707, 1984.
Zoller, M. et al, Nucleic Acids Res., vol. 10, pp. 6487–6500, 1982.
Opdennaker, G. et al, *EMBO Workshop on Plasminogen Activators*, Amalpi, Italy, Oct. 14–18, 1985.

Primary Examiner—Garnette D. Draper
Assistant Examiner—Marianne Porta Allen
Attorney, Agent, or Firm—Spencer, Frank & Schneider

[57] ABSTRACT

Novel polypeptide compositions based on the amino acid sequence of tissue plasminogen activator (tPA) are provided having improved properties over natural tissue plasminogen activator. Particularly, enhanced specific activity, reduced response to inhibition by plasminogen activator inhibitor, fibrin stimulation of plasminogenolytic activity and/or enhanced affinity to fibrin surfaces are provided by modifying one or more loci by deletions or substitutions. One or both of the N- or C-termini may be modified.

15 Claims, No Drawings

PEPTIDE PLASMINOGEN ACTIVATORS

CROSS REFERENCE TO RELATED APPLICATION

This application is a continuation-in-part of our application Ser. No. 812,879 filed Dec. 23, 1985, now abandoned the entire specification of which is incorporated herein by reference.

BACKGROUND OF THE INVENTION

1. Field of the Invention

Tissue plasminogen activator (tPA) is a serine protease involved with the dissolution of blood clots. The molecule has a number of distinct regions which display amino acid sequence homology with other naturally occurring polypeptides. Beginning at the N-terminus is a region homologous to fibronectin. The next region has homology with various growth factors. The growth factor region is followed by two kringle regions. Finally, there is the active site finding analogy with other serine proteases.

There are at least four different properties associated with tissue plasminogen activator and its ability to lyse blood clots in vivo. The first is the specific activity of the protease function in cleaving plasminogen to produce plasmin which in turn degrades fibrin. The second property is the sensitivity to inhibition by plasminogen activator inhibitor. The third property is the fibrin dependence of plasminogen activator for its plasminogenolytic activity. The fourth is the binding of tPA to fibrin surfaces. Each of these factors plays a role in the rapidity and the specificity with which plasminogen activator will cleave plasminogen to plasmin in the presence of blood clots. It would therefore be of substantial interest to be able to produce polypeptides having tissue plasminogen activator activity which will provide for improved properties in one or more of these categories.

2. Brief Description of the Relevant Literature

The use of mutagenesis to enhance native properties of a naturally occurring protein has been reported by Craik et al., *Science* (1985) 228:291; Rosenberg et al., *Nature* (1984) 312:77–80 and Wilkinson et al., *Nature* (1984) 307:187–188. Andreasen et al., *EMBO J.* (1984) 3:51–56, report that clipping at the cleavage site of tPA is necessary for protease activity. Ny et al., *Proc. Natl. Acad. Sci. USA* (1984) 81:5355, report the structure of human tPA and the correlation of introns and exons to functional and structural domains. A. J. van Zonneveld et al., Abstract from ISTH Meeting, July 14–19, 1985, report on the relationship between structure and function of human tissue-type plasminogen activator. *J. Biol Chem.* (1986) 261:14214–14218. Opdenakker et al., *EMBO Workshop on Plasminogen Activation* (Amalfi, Italy, Oct. 14–18, 1985) report the effect of removal of carbohydrate side chains on tPA activity. Loskutoff et al., *Proc. Natl. Acad. Sci. USA* (1983) 80:2956–2960, and Loskutoff, *Thrombos. Haemostos, THHADQ,* 54(1):118 (S699) describe the properties of plasminogen activator-inhibitor.

SUMMARY OF THE INVENTION

Polypeptides having plasminogen activator activity are provided by employing deletions or substitutions, individually or in combination in the tPA molecule, where glycosylation is changed, the C-terminus truncated and the cleavage site modified. The resulting products find use in lysis of fibrin clots and prevention of blood clot formation by activating plasminogen. These polypeptides may be produced by expression of mutated genes created by site-directed mutagenesis.

DESCRIPTION OF THE SPECIFIC EMBODIMENTS

Novel polypeptides having enhanced properties as plasminogen activators are provided including DNA coding sequences coding for such polypeptides, expression cassettes containing such sequences for expression in an appropriate host, hosts capable of expressing the novel polypeptides and methods for producing the novel polypeptides. The novel polypeptides involve changes at at least one glycosylation site, at least one change at the cleavage site in the region from 272 to 280, particularly in the sequence $Phe_{274}$-$Arg_{275}$-$Ile_{276}$-$Lys_{277}$ (FRIK), and/or truncation at one or both termini of the molecule particularly the C-terminus. Where the only modification is at the glycosylation sites, both glycosylation sites at 117–119 and 184–186 will be modified, either the same or different. (The numbering of the amino acids which is employed is based on that reported by Pennica et al., *Nature* (1983) 301:214–221, beginning at serine in the sequence glycine-alanine-arginine-serine-tyrosine.) By introducing these changes in polypeptides having tissue plasminogen activator activity and derived from human tissue plasminogen activator improved physiological properties can be achieved.

The novel polypeptides exhibit enhanced proteolytic and specifically plasminogenolytic activity, reduced sensitivity to plasminogen activator inhibition, increased affinity for fibrin and/or increased fibrin dependence for plasminogenolytic activity.

The first change of interest is the modification of at least one glycosylation site at amino acids 117–119, 184–186 and 448–450, where either the asparagine is changed, conservatively or non-conservatively, or the serine or threonine is changed non-conservatively, particularly by gly, ala or val. Of particular interest are the glycosylation sites at 117–119 and 184–186. Mutations of interest include substituting asparagine with other amino acids, preferably glutamine, valine, leucine, isoleucine, alanine or glycine, more preferably glutamine or substituting serine or threonine with other amino acids, preferably alanine, valine, or methionine, that is, aliphatic amino acids of from 3 to 5 carbon atoms lacking mercapto or neutral hydroxyl substituents. Substituting asparagine with glutamine at the glycosylation sites at 117 and 184 is of special interest.

Depending upon the desired change in the properties of the mutated product, either conservative or non-conservative changes may be involved. Conservative changes are indicated by the amino acids included within a semi-colon. G, A; V, I, L; D, E; K, R; N, Q; S, T; and F, W, Y; where an amino acid in one grouping is substited by an amino acid in another grouping or an amino acid which is not indicated above, such change will be considered non-conservative.

It is found that specific activity can be enhanced by reducing the amount of glycosylation of the molecule, particularly at the glycosylation sites in the kringle structures, more particularly the first two glycosylation sites proceeding from the N- to the C-terminus.

Various lesions may be introduced at the glycosylation sites, such as substitutions, or the like, to change the glycosylation site triad so as to destroy the glycosylation site. For example, glycosylation sites at 117–119 and 184–186 and 448–450 may be modified, either the same or differently.

The next area of interest is modification of the cleavage site which occurs at amino acids 274 to 278. Of particular interest are conservative changes, such as substituting lysine at 277 with arginine. Other substitutions include replacing isoleucine at 276 with valine, leucine, glycine or alanine. It is found that a specific modification at the cleavage site can reduce sensitivity to plasminogen activator inhibition, so that in vivo, the polypeptide will have an increased activity as compared to the wild-type tissue plasminogen activator in the presence of a naturally inhibiting amount of plasminogen activator inhibitor.

The third change of interest is truncation of the N- or C-terminus, particularly the C-terminus by at least 1 amino acid and up to 25 amino acids, usually up to 10 amino acids, more usually up to 3 amino acids. The N-terminus may be truncated by from 1 to 5 amino acids, starting with ser, followed by tyr, more particularly from 1 to 3 amino acids.

Truncation at the C-terminus provides for enhanced fibrin dependence, so that greater specificity of the tissue plasminogen activator may be achieved. By increasing fibrin dependence, the amount of plasminogen which is cleaved to plasmin away from a clot will be substantially reduced, avoiding side effects of the plasmin.

The novel polypeptides of the invention may be produced by combining two, three or more of the changes described above. For example, in addition to substituting aspargine with glutamine at the glycosylation sites at 117 and 184, an example of the first type of change, the cleavage site at 277 may be modified by substituting lysine with arginine (an example of the second type of change) or the sequence Met 525 to Pro 527 may be truncated (an example of the third type of change).

In some instances, rather than truncating the tPA the chain may be extended or terminal amino acids extended, generally from about 1 to 12 amino acids at one or both of the N- and C-termini. Added amino acids may serve as linkers, provide a particular immune response, modify the physical properties of the molecule, or the like.

The DNA sequences encoding for the subject polypeptides may be prepared in a variety of ways, using chromosomal DNA including introns, cDNA, synthetic DNA, or combinations thereof. The desired mutations may be achieved by cloning the gene in an appropriate bacterial host using a single-stranded bacteriophage vector or double stranded plasmid vector and then using a mismatched sequence substantially complementary to the wild-type sequence but including the desired mutations, such as transversions, transitions, deletions, or insertions. Alternatively, where convenient restriction sites exist, one could excise a particular sequence and introduce a synthetic sequence containing the mutations. Other techniques which may be employed are partial exonucleolytic digestion of a double-stranded template or in vitro heteroduplex formation to expose partially single-stranded regions for oligonucleotide-directed mutagenesis.

Of particular interest is oligonucleotide directed mutagenesis. (Zoller and Smith, *Methods Enzymol.* (1983) 100:468–500.)

Appropriate oligonucleotide sequences containing the mismatches, deletions or insertions are prepared generally having about 20 to 100 nucleotides (nt), more usually 20 to 60 nt. The sequences can be readily prepared by synthesis and be cloned in an appropriate cloning vector. The olgonucleotides are annealed to a purified template of the tPA gene or tPA analog for site directed mutagenesis. The mutations may be introduced individually, where the sites of mutation are separated by about 10 base pairs (bp), more usually by about 20 bp. Mutations at different sites may be introduced in a single step or successive steps, after each mutation establishing the existence of the mutation and its effect on the activity of the tPA analog.

In designing mutagenesis primers, a number of considerations are involved. Usually, the length of the primer is chosen to yield less than about 95% complementarity with a target template but greater than about 85%. This provides an additional advantage in permitting facile plaque screening with a mutagenesis primer. Where mutagenesis primers generate deletions, normally there will be at least about 20 base pair complementarity on each side of the deletion. Also, the primer should provide approximately equal melting temperatures on either side of the locus of mutation. There is the further consideration that primers should be selected so as to minimize, if not eliminate, priming events at inappropriate sites on the template. In effect, complementarity should be less than 70%, preferably less than 60%, at any site other than the mutagenesis locus. Thus must be considered not only for the gene of interest, but also for the cloning vector. Of particular concern is complementarity at the 3' end of the primer.

Conveniently, the vector will be a single-stranded circular DNA virus, e.g., M13, particularly where modified for purposes of use as a vector. A convenient vector virus is M13mp9. The mutagenesis primer is combined with the template and vector under annealing conditions in the presence of an appropriate polymerase lacking correction capability, such as the Klenow fragment or T4 DNA polymerase in the presence of the necessary nucleotides and T4 DNA ligase, whereby the cyclic, gene carrying vector is replicative to provide for the double-stranded replication form. The double-stranded DNA may then be introduced into an appropriate cell. By providing for a lytic vector, plaques are obtained which may be screened with a primer for the presence of the mutagenized tPA or tPA analog. Usually, at least two repetitive screenings will be required, employing increased sensitivity so as to enhance the probability of having the correct sequence for the mutagenized product.

The putative positive clones may then be purified, e.g., plaque purified, electrophoretically purified, or the like, and then sequenced.

For sequencing, sequencing primers are designed which will be at least about 20 to 30 bases in length and will anneal at a position at least about 55 bases away from the site of the mutation locus. In order to have reasonable assurance of the correct sequence, it is desirable that a region be sequenced which includes at least about 50 bases either side of the mutation locus.

Once the correctly mutagenized gene is obtained, it may be isolated and inserted into an appropriate expression vector for expression in an appropriate host.

A wide variety of expression vectors exist for use in mammalian, insect and avian hosts. See, for example, those described in EPA 0,092,182, which is incorporated herein by reference. Of particular interest are mammalian expression vectors, which employ viral replicons, such as simian virus, bovine papilloma virus, adenovirus, or the like.

The transcriptional and translational initiation and termination regulatory regions may be the regions naturally associated with the tPA gene or regions derived from viral structural genes or regions derived from host genes. A large number of promoters are available, such as the SV40 early and late promoters, adenovirus major late promoter, β-actin promoter, human CMV Immediate Early [IE1] promoter, etc. Desirably, the promoters will be used with enhancers to provide for improved expression.

In many instances it will be desirable to amplify the tPA expression construct. For amplification or for other reasons, it may be desirable to have the expression construct integrated into the genome. Toward this end the construct will either be joined to an unstable replication system, e.g., yeast a rs1, or lack a replication system. For integration, see, for example, Axel and Wigler, U.S. Pat. No. 4,399,216. Usually a marker expression construct will be in tandem with the subject expression construct, which marker may be the same or different from the amplifying gene. This can be achieved by having the tPA in tandem with an expression construct, functional in the same host as the tPA expression construct, and encoding such amplifiable genes as DHFR (dihydrofolate reductase), TK (thymidine kinase), MT-I and -II (metallothionein, e.g. human), ODC (ornithine decarboxylase). By stressing the host in accordance with the amplifiable gene, e.g., methotrexate with DHFR, the subject expression constructs may be amplified.

Depending upon the particular hosts and signal sequences used, the tPA analog which is expressed may be retained in the host cell in the cytoplasm or be secreted. Where retained in the cytoplasm, the tPA analog may be isolated by lysis of the host cell using standard methods and purified by extraction and purification, preferably by employing electrophoresis, chromatography, or the like. Where the tPA is secreted, the secreted tPA may be isolated from the supernatant in accordance with conventional techniques including affinity chromatography.

The combined properties of the polypeptides employed in this invention are superior to naturally occurring plasminogen activators like tPA. These polypeptides will have at least 0.6 times, often at least 0.7 times, usually at least 1.0 times, generally from about 1.1 to 7.0 times, and preferably from about 6.2 to 7.0 times the specific activity of natural tPA. The fibrin dependence of the activity will be at least 0.4, often at least about 0.6 times, generally at least about 0.7 times, and preferably at least about 1 to 2.5 times, particularly 1.3 to 2.5 times the naturally occurring tPA. Susceptibility to plasminogen activator inhibitor will usually be not greater than natural tPA, preferably about 5% less, based on the sensitivity of the natural tPA, more preferably from about 10% less ranging up to about 90% less, and particularly about 25% to 90% less than natural tPA. The subject compounds will usually be superior to wild-type tPA in at least one aspect. (See the Experimental section for test procedures.)

Of particular interest are polypeptides having tissue plasminogen activity, having substantially the same amino sequence as human tPA (fewer than 10 number %, usually fewer than 5 number % differences including substitutions, deletions and insertions). These polypeptides will have at least one of: (a) specific activity at least about 0.6 times, often at least about 0.7 times, usually at least about 1.0 times, generally from about 1.1 to 7.0 times, and preferable from about 6.2 to 7.0 times the specific activity of natural tPA; (b) fibrin dependence at least 0.4 times, often at least about 0.6 times, generally at least about 0.7 times, and preferably at least about 1.0 to 2.5 times, particularly about 1.5 to 2.5 times the naturally occurring tPA; (c) reduced susceptibility to inhibition by human plasminogen activator inhibitor of preferably about 5%, compared to the sensitivity of natural tPA, more preferably about 10% less ranging up to about 90% less, and particularly about 25% to 90% less than natural tPA.

The subject polypeptides may be used in a variety of ways in the prophylactic or treatment for various vascular conditions or diseases specifically to protect a mammalian, particularly a human, host from thrombus formation. It may therefore be administered during operations where the host may be susceptible to blood clotting, or for treatment of thrombotic patients, to dissolve blood clots which may have formed in deep vein thrombosis, pulmonary embolism, cranial and coronary thrombosis.

The subject compounds may be administered enterally or parenterally, especially by injection or infusion. These compounds may be administered in an effective amount in a physiologically acceptable carrier, such as water, saline, or appropriate buffer systems in the presence of protein stabilizing substances selected from the group of gelatin, gelatin derivatives, protective proteins such as albumin, sugar, sugar alcohol, or amino acids solely or in combination with other therapeutic drugs, especially for vascular diseases.

The following examples are offered by way of illustration and not by way of limitation.

EXPERIMENTAL

Materials and Methods

Mutagenesis was achieved employing the procedure described by Zoller and Smith, *Meth. Enzymol.* (1983) 100:468–500, modified as described below. Synthetic DNA mutagenesis and sequencing primers were prepared by automated oligonucleotide synthesis on a silica support as described by Urdea et al., *Proc. Natl. Acad. Sci. USA* (1983) 80:7461–7465, using N,N-diisopropyl phosphoramidities. Sequencing primers were designed for sequencing by the dideoxynucleotide chain termination method in bacteriophage M13 (F. Sanger, S. Nicklen and A. R. Coulson, *Proc. Natl. Acad. Sci. USA* (1977) 74:5463). The sequencing primers were designed to be complementary to M13mp9 recombinant templates, generally of 20 to 30 bases in length and to anneal at a position at least 55 bases away from the mutation locus. The following Table indicates the oligomers employed for mutagenesis and sequencing.

TABLE I

| | Mutagenesis primers |
|---|---|
| 1a. | CGCGCTGCTC̲TGCCAGTTGGT |
| 1b. | CTGACCCCT̲GCCCAAAGTAGC |
| 2. | TTGAGGAGTCGGGTGTTCCTGGTCA/ GTTGTCACGAATCCAGTCTAGGTAG |
| 3. | AGAGCCCTCCTC̲TGATGCGA |
| 4. | CTC̲TGATTT̲T̲AAACTGAGGCTGGCTGTA |
| 5. | GACTGTTCTC̲TGAAGTAAATG |

| | Effect of mutation |
|---|---|
| 1. | Asn 117 → Gln, Asn 184 → Gln |
| 2. | Delete Met 525 through Pro 527 |
| 3. | Lys 277 → Arg |
| 4. | Lys 277 → Arg, Arg 275 → Lys |
| 5. | Asn 117 → Gln, Asn 184 → Gln, Asn 448 → Gln |

| | Sequence primers |
|---|---|
| 1a. | ACCTTGCCTATCAGGATCAT |
| 1b. | CGAATCGCCCTGGCAGGCGTC |
| 2. | GTGGGTCTGGAGAAGTCTGTA |
| 3, 4. | GCACAGGAACCGCTCTCCGGG |
| 5. | TCGATCTGGGTTTCTGCAGTAGTTGTGGTT |

Note:
N̲ denotes substitution from wild type
/ denotes deletion

Mutagenesis of M13/tPA recombinants was performed using purified templates by annealing and extending the appropriate primer with the Klenow fragment or T4 polymerase. Mutant 1 was obtained utilizing both primers 1a and 1b in a single round of mutagenesis. Mutant 4 was obtained using a template derived from mutant 3 in the presence of 125 μg/ml gene 32 protein and a helper primer which binds to M13 sequences adjacent to the insert. The effect of primer 4 (Arg 275→ Lys) was combined with the effect of primer 3 (Lys 277→Arg) to produce the two mutation sites shown above. Mutant 5 was obtained using a template derived from mutant 1. The effect of primers 1a and 1b (Asn 117→Gln, Asn 184→Gln) was combined with the effect of primer 5 (Asn 448→Gln) to produce the three mutation sites shown above. Following transfection of JM101 cells (Zoller and Smith, supra), plaques were grown at a density of 200–1000/ plate and were lifted onto filters and screened by hybridization with the appropriate mutagenesis primer or probe. Ten to 40 percent of these plaques were initially identified as putative positive candidates. Rescreening of approximately six of these putatives from each experiment by dot blot hybridization of phage yielded strong candidates. These phage were plaque purified by replating at low density, transferring onto nitrocellulose filters and rehybridizing with primers. The DNA sequence of putative positive clones was determined using suitable primers and template preparations.

Once the mutagenized locus and flanking segments (i.e., at least 50 bases) were confirmed by DNA sequence analysis, replicative form (RF) DNAs were digested with SalI restriction endonuclease and inserted into the mammalian expression vector pSV7d previously digested with SalI and treated with alkaline phosphatase. The vector provides an SV40 early promoter and enhancer for expression of the tPA cDNA, an SV40 polyadenylation site, and an SV40 origin of replication for use of the vector in COS cells.

The plasmid pSV7d was constructed as follows: the 400 bp BamHI/HindIII fragment containing the SV40 origin of replication and early promoter was excised from pSVgtI (Mulligan, R. et al., *J. Mol. Cell Biol.* 1:854–864 (1981)) and purified. The 240 bp SV40 BclI/BamHI fragment containing the SV40 poly A addition site was excised from pSV2/dhfr (Subramani et al., *J. Mol. Cell Biol.* 1:584–864 (1981)) and purified. The fragments were fused through the following linker:

```
                  Stop Codons
                  1    2    3
5' - AGCTAGATCTCCCGGGTCTAGATAAGTAAT- 3'
        TCTAGAGGGCCCAGATCTATTCATTACTAG
HindIII  BglII SmaI  XbaI       BclI overhang.
```

This linker contains five restriction sites, as well as stop codons in all three reading frames. The resulting 670 bp fragment containing the SV40 origin of replication, the SV40 early promoter, the polylinker with stop codons and the SV40 polyadenylation site) was cloned into the BamHI site of pML, a pBR322 derivative with about 1.5 kb deletion (Lusky and Botchan, Cell 36:391 (1984)), to yield pSV6. The EcoRI and EcoRV sites in the pML sequences of pSV6 were eliminated by digestion with EcoRI and EcoRV, treated with Bal31 nuclease to remove about 200 bp on each end, and finally religated to yield pSV7a. The Bal31 resection also eliminated one BamHI restriction site flanking the SV40 region, approximately 200 bp away from the EcoRV site. To eliminate the second BamHI site flanking the SV40 region, pSV7a was digested with NruI, which cuts in the pML sequence upstream from the origin of replication. This was recircularized by blunt end ligation to yield pSV7b.

pSV7c and pSV7d represent successive polylinker replacements. Firstly, pSV7b was digested with StuI and XbaI. Then, the following linker was ligated into the vector to yield pSV7c:

```
    BglII EcoRI   SmaI     KpnI  XbaI
5'-AGATCTCGAATTCCCCGGGGGTACCT
   TCTAGAGCTTAAGGGGCCCCCATGGAGATC
```

Thereafter, pSV7c was digested with BglII and XbaI, and then ligated with the following linker to yield pSV7d:

```
    BglII EcoRI  SmaI XbaI   BamHI SalI
5' - GATCTCGAATTCCCCGGGTCTAGAGGATCCGTCGAC
        AGCTTAAGGGGCCCAGATCTCCTAGGCACGTGGATC
```

The appropriate orientation of the cloned fragments within the vector was deduced by restriction site analysis. The mutations were reconfirmed by restriction analysis for SalI and EcoRI and by Southern blotting of such fragments using appropriate, highly specific probes directed at the locus of the mutation.

Combination Mutants

Four combination mutants: mutant 6 which contains both mutations 1 and 2, and mutant 7 which contains both mutations 1 and 3, mutant 8 which contains both mutations 2 and 3, and mutant 9 contains all three mutations 1, 2, and 3, were constructed using recombinant DNA technology. Each of the mutations is separated by convenient restriction enconuclease sites which facilitated the assembly of the desired mutations from fragments of the previously isolated mutants 1, 2, and 3. The specific strategy employed in the construction of each mutant is described below.

Large scale plasmid preparations were carried out for all of the mutant constructions described. The DNA was used for transfections into tissue culture cells.

Mutant 6 (1&2)

The 1.72 kilobase (kb) BamHI to BstEII fragment of mutant 1 contains both of the mutated sites Asn 117→Gln and $Asn_{184}$→Gln This fragment was ligated to the 3.38 kb BamHI to BstEII fragment of mutant 2 which contains the desired mutation, the deletion of $Met_{525}$ through $Pro_{527}$. This ligation mixture was used to transform competent E. coli. A few of the resultant ampicillin resistant colonies were grown up and their DNA was screened by size and by DNA hybridization analysis of Southern blots of the DNA with $^{32}p$ end labeled oligonucleotide probes specific to each mutated region. Thus clones were scored as positive if they hybridized to each of the two individual mutant 1 region oligonucleotides and the mutant 2 specific probe. This screening method was used for each of the constructs with the substitution of the appropriate oligonucleotide probe(s) for each new construction. The specific oligonucleotides utilized are listed previously.

Mutant 7 (1&3)

The 2.95 kb ScaI fragment of mutant 1 which contains both of the mutated sites, was ligated to the 2.15 kb ScaI fragment of mutant 3 which contains the change $Lys_{277} \rightarrow$ Arg. Screening of the new construction was accomplished using oligonucleotides specific to the mutant 3 change and to each of the mutant 1 alterations.

Mutant 8 (2&3)

The 3.38 kb BamHI to BstEII fragment of mutant 2 containing the desired alteration was ligated to the 1.72 kb BamHI to BstEII fragment of mutant 3, containing the $Lys_{277} \rightarrow Arg$ mutation. Screening for the proper recombinants was accomplished using oligonucleotides specific to each mutation.

Mutant 9 (1&2&3)

The strategy for making the triple mutant involved using one of the newly constructed double mutants, mutant 7. This plasmid was cleaved with BamHI and BstEII, and the 1.72 kb fragment containing both mutations was isolated. Plasmid DNA from mutant 2 was digested with the same restriction enzymes and the 3.38 kb piece (containing the mutation) was isolated.

These two fragments were ligated, and the ligation mix was used to transform competent E. coli. Screening for the correct triple mutants was done as described above, using oligonucleotides specific to each mutated site in the DNA.

Mammalian Cell Transfections

COS-7 cells (Gluzman, *Cell* (1981) 23:175) were transfected with the pSV7d tPA expression plasmids using a modification of the procedure described by Graham and van der Eb, *Virology* (1973) 52:456–467. The samples were added to the dishes in duplicate and allowed to settle onto the cells for 6 h in a carbon dioxide incubator (37° C.). Six hours later, the supernatants were aspirated, the cells rinsed gently with Ca- and Mg-free phosphate-buffered saline (PBS-CMF), and the dishes exposed to 15% glycerol as an adjuvant for 3.5–4 min. After rinsing and feeding with DMEM medium, supplemented with 4.5 mg/ml glucose, 3.7 mg/ml $Na_2CO_3$, 292 µg/ml glutamine, 110 µg/ml sodium pyruvate, 100U/ml penicillin, 100U/ml streptomycin and 10% fetal calf serum (FCS), the medium was replaced with medium lacking the fetal calf serum. Twelve hours after serum withdrawal, cells were assayed for expression of tPA, using the casein-plasminogen-agar overlay described below. Maximum expression was observed between 36 and 48 h after the start of the transfection.

CHO dhfr⁻ cells (Urlaub and Chasin, *Proc. Natl. Acad. Sci. USA* (1980) 77:4216) were plated at a density of $5 \times 10^5$ to $10^6$ cells per 10cm dish the day prior to transfection in nutrient medium (F12 supplemented with 1.18 mg/ml $Na_2CO_3$, 292 µg/ml glutamine, 110 µg/ml sodium pyruvate, 100U/ml penicillin, 100U/ml streptomycin, 150 µg/ml proline and 10% FCS). The above-described transfection procedure was employed with the modification that the tPA expression plasmid was mixed with a plasmid bearing as a selectable marker, a dhfr gene driven by the adenovirus major late promoter, followed by co-precipitation of the plasmids in calcium phosphate. The plasmid bearing the dhfr gene was constructed by fusing the major late promoter from adenovirus-2 (Ad-MLP, map units 16–17.3) to the mouse dhfr cDNA at the 5' end. DNA coding for the intron for SV40 small t antigen and the SV40 early region polyadenylation site was obtained from pSV2-neo (Southern and Berg, *J. Mol. Appl. Genet.* (1982) 1:327–341), and fused to the 3' end of the dhfr cDNA. These three segments were subcloned into pBR322 to obtain the plasmid Ad-dhfr. Forty-eight hours after the addition of DNA to the cells, the cells were split 1:20 into selective medium (DMEM supplemented with proline and fetal calf serum as above, or with dialyzed fetal calf serum). After growth in selective medium for 1–2 weeks, colonies appeared and were assayed for production of tPA by the casein-plasminogen-agar overlay assay and in casein-plasminogen plates for quantitation.

Cell lines from each mutant were grown to confluency in 200 cm² dishes and incubated for 24 h periods in serum-free medium (DMEM), and supernatants were processed as described below to purify the polypeptides with plasminogen activator activity.

The following procedures were employed for determining the activity of the nine polypeptides described above.

In order to determine the specific activity of the mutant proteins, it was necessary to quantify the antigen concentration of the samples. An EIA-kit using polyclonal antibodies (American Diagnostica, Inc., Greenwich, Conn.) was employed. The test was performed strictly under the conditions described in the protocol provided with the kit and five dilutions of each sample were analyzed. The results were expressed as the average of at least three measurable dilutions.

Concentration of mutant proteins with plasminogen activivator activity

All cell culture supernatants were made 0.01% Tween 80™ and 0.01% Na-azide. The supernatants (50 ml) were then incubated for 30 min at room temperature in the presence of 3 ml Heparin-Sepharose®. The Heparin-Sepharose suspensions were filled into columns and extensively washed with 20 ml of a buffer containing 0.1M phosphate, 0.01% Tween 80™, pH 7.5. Finally, the tPA activity was eluted with a buffer containing 0.05M tris-HCl, 1M KSCN and 0.01% Tween 80™, pH 7.5. The eluates were then dialyzed at 4° C. for 16 h against 5L of a phosphate-buffer (0.05M, pH 7.5) containing 0.01% Tween 80™ and 0.01% Na-azide. The tPA samples were frozen in 1 ml portions at −25° C.

Clot lysis test (CLT)

The clot lysis test was performed using a "KC 10-Koagulometer" (Amelung, FRG) which has been modified in order to record the lysis time instead of the coagulation time.

All reagents were preincubated at 37° C. The tPA standard, the polypeptide test samples and fibrinogen were diluted to the required concentrations in a phosphate-buffer (0.67M) containing 1% Haemaccel™ (pH 7.4). 0.2 ml of the tPA standard or of the samples were mixed with 0.2 ml human plasminogen (10 CTA/ml), 0.5 ml bovine fibrinogen (0.15%) and finally 0.1 ml thrombin (10 IU/ml). The lysis time was recorded and expressed in tPA units using a calibration curve. The activity of each mutant protein was analyzed at least three times, and the average was calculated. Four dilutions of the tPA standard were run with each of the samples to be analyzed.

Plasminogenolytic assay

The plasminogenolytic activity of the mutant proteins was analyzed using the parabolic assay described by Ranby et al., *Thromb. Res.* (1982) 27:743–749. All reagents were preincubated at 37° C. 0.1 ml of the tPA standard or of the tPA samples were mixed with 0.5 ml buffer (0.1M tris-HCl, pH 7.5 containing 0.1% Tween 80™ and 0.01% Na-azide), 0.1 ml substrate (S 2251 (H-D-Val-Leu-Lys-(para-nitroanilide) (Kabi AB, Sweden)), 3 mM), 0.1 ml human plasminogen (1 CTA/ml) and 0.1 ml fibrin degradation products (10 mg/ml). Finally, the mixture was incubated for 45 min at 37° C. The reaction was stopped by addition of 0.1 ml acetic acid (50%) and the optical density was read at 405 nm. The calibration curve obtained was used to convert the optical density of the samples in units. The results were expressed as the average of at least five measurable dilutions.

Additionally, the same test was performed in the absence of fibrin degradation products (FDP). In this case, 0.6 ml buffer were required instead of 0.5 ml. Fibrin dependence of the activity The influence of the co-factor—fibrin or fibrin degradation products (FDP)—on the ability of tPA and mutant polypeptides to activate plasminogen into plasmin was expressed as the ratio between the activity obtained in the clot lysis test or in the fibrin-dependent plasminogenolytic assay and the activity determined in the fibrin-independent plasminogenolytic assay.

Fibrin-affinity

Preparation of fibrin clots 0.2 ml aliquots of human fibrinogen (0.3%) were disposed in plastic tubes and mixed with 0.005 ml bovine thrombin (500 IU/ml). The mixtures were allowed to stay for 30 min at 37° C. After completion of the reaction the clots were carefully removed and incubated for 30 min at 37° C. in 2 ml buffer (0.1M tris-HCl), pH 8.0) containing antithrombin III (3 IU/ml) and heparin (40 IU/ml). Finally, the clots were removed and dialyzed twice for 20 min against 50 ml buffer (0.05M tris-HCl, 0.1M NaCl, pH 7.5). Before use, the clots were freed of surrounding solution.

Test procedure

All samples were first diluted to 200 ng/ml in a Tris-buffer (0.1M, pH 7.5) containing 0.1% Tween 80™. Afterwards the samples were diluted to a final concentration of 100 ng/ml in the same buffer containing 5% human albumin. Subsequently, 0.4 ml of the samples were incubated for 10 min at room temperature in the presence of one fibrin clot. Finally, the solution was removed and the antigen concentration in the fluid phase was determined with EIA. This experiment was performed twice for each sample.

Inhibition test

The samples were diluted in a Tris-buffer (0.1M, pH 7.5) containing 0.1% Tween 80™ to a final concentration of 100 ng/ml.

0.2 ml aliquots were then mixed with 0.2 ml of a solution containing the plasminogen activator inhibitor at a concentration of 65 urokinase inhibitory units/ml. In control experiments the polypeptide samples described above were mixed with 0.2 ml buffer (100%). The mixtures were incubated for 10 min at 37° C. At the end of the incubation time, the samples were rapidly diluted and the residual activity analyzed with the fibrin-dependent plasminogenolytic assay. The inhibition test was performed twice for each sample. The inhibition susceptibility is expressed as the percent activity that is inhibited.

The plasminogen activator inhibitor has been purified from human placenta. The inhibitory fraction does not contain any proteolytic activity nor plasmin, thrombin or trypsin inhibitory activity.

The values from the above described assays for the mutant proteins are listed in Table II.

TABLE II

| | Biochemical characterization of the mutants | | | | | | | | | |
|---|---|---|---|---|---|---|---|---|---|---|
| | Specific activity $10^3$ U/mg | | | | | | Fibrin dependence of the activity | | Inhibitor | Binding |
| | | $CLT_m^{(2)}$ | | $F\text{-}Plg._m^{(2)}$ | | $Plg._m^{(2)}$ | $CLT^{(5)}$ | $F\text{-}Plg.^{(6)}$ | susceptibility | to fibrin |
| Mutant | $CLT^{(1)}$ | $CLT_w$ | $F\text{-}Plg.^{(3)}$ | $F\text{-}Plg._w$ | $Plg.^{(4)}$ | $Plg._w$ | Plg. | Plg. | (%) | (%) |
| 1 | 1118 | 2.74 | 1215 | 2.87 | 493 | 2.13 | 1.30 | 1.32 | 26.1 | 36 |
| 2 | 404 | 0.99 | 307 | 0.73 | 81 | 0.35 | 2.77 | 2.00 | 35.2 | 39 |
| 3 | 288 | 0.71 | 284 | 0.67 | 257 | 1.11 | 0.61 | 0.58 | 12.1 | 33 |
| 4 | 232 | 0.57 | 214 | 0.51 | 169 | 0.73 | 0.78 | 0.68 | 17.7 | 34 |
| 5 | NA | 3.2 | NA | 2.8 | NA | 7.4 | 0.43 | 0.38 | 20.3 | 46 |
| 6(1&2) | NA | 6.50 | NA | 4.70 | NA | 3.40 | 1.90 | 1.38 | 14.2 | 60 |
| 7(1&3) | NA | 2.80 | NA | 1.80 | NA | 4.10 | 0.70 | 0.44 | 8.3 | NA |
| 8(2&3) | NA | 1.3 | NA | 0.8 | NA | 1.9 | 0.68 | 0.42 | 12.5 | 63 |
| 9(1&2&3) | NA | 1.5 | NA | 0.6 | NA | 1.0 | 1.5 | 0.6 | 13.4 | 67 |
| Wild Type | 408 ± 136 | 1 ± 0.33 | 423 ± 47 | 1 ± 0.11 | 232 ± 67 | 1 ± 0.28 | 1 ± 0.33 | 1 ± 0.26 | 41 ± 2 | 28 ± 5 |

NA - Not Available
[1] clot lysis test
[2] ratio:
activity of mutant protein (m)
activity of wild type tPA (w)
[3] Fibrin-dependent plasminogenolytic assay
[4] Fibrin-independent plasminogenolytic assay
[5] ratio:
activity in CLT
activity in fibrin-independent plasminogenolytic assay
[6] ratio:
activity in fibrin-dependent plasminogenolytic assay
activity in fibrin-independent plasminogenolytic assay It is evident from the above results that substantial advantages can be achieved by making changes in the wild-type tPA amino acid sequence. Thus, not only can activity be increased, but at the same time sensitivity to plasminogen activator inhibitor can be decreased, so that overall a very substantial increase in effective activity can be achieved in vivo. Also, the enzyme can be made substantially more specific in providing for enhanced fibrin dependence, so that it has substantially reduced activity in the absence of clots. Thus, one can administer lower amounts of these polypeptides with plasminogen activator activity, so as to minimize the level in the blood stream of the protein (or enzyme) and substantially diminish the undesirable side effects of tPA, while providing for increased activity against clots.

Although the foregoing invention has been described in some detail by way of illustration and example for purposes of clarity of understanding, it will be obvious that certain changes and modifications may be practiced within the scope of the appended claims.

What is claimed is:

1. A human tissue plasminogen activator capable of dissolving clots and having at least one improved property selected from the group consisting of improved plasminogenolytic specific activity, increased fibrin dependence, and decreased plasminogen inhibitor susceptibility, said human tissue plasminogen activator having the lysine at amino acid position 277 substituted with arginine and having from 3 to 25 amino acids deleted from the C-terminus.

2. A human tissue plasminogen activator capable of dissolving clots and having at least one improved property selected from the group consisting of improved plasminogenolytic specific activity, increased fibrin dependence, and decreased plasminogen inhibitor susceptibility, said human tissue plasminogen activator having from 3 to 25 amino acids deleted from the C-terminus and having at least one of the group consisting of asparagine 117, asparagine 184 and asparagine 448 substituted with glutamine.

3. A human tissue plasminogen activator capable of dissolving clots and having at least one improved property selected from the group consisting of improved plasminogenolytic specific activity, increased fibrin dependence, and decreased plasminogen inhibitor susceptibility, said human tissue plasminogen activator having the lysine at amino acid position 277 substituted with arginine and having at least one of the group consisting of asparagine 117, asparagine 184 and asparagine 448 substituted with glutamine.

4. A human tissue plasminogen activator capable of dissolving clots and having at least one improved property selected from the group consisting of improved plasminogenolytic specific activity, increased fibrin dependence, and decreased plasminogen inhibitor susceptibility, said human tissue plasminogen activator having the lysine at amino acid position 277 substituted with arginine, having from 3 to 25 amino acids deleted from the C-terminus and having at least one of the group consisting of asparagine 117, asparagine 184 and asparagine 448 substituted with glutamine.

5. The human tissue plasminogen activator of any one of claims 1, 2 or 4 having Met-525 to Pro-527 deleted.

6. The human tissue plasminogen activator of any one of claims 2, 3 or 4, having at least two of the group consisting of asparagine 117, asparagine 184 and asparagine 448 substituted with glutamine.

7. The human tissue plasminogen activator of either of claim 3 or claim 4 having each of asparagine 117, asparagine 184 and asparagine 448 substituted with glutamine.

8. A nucleic acid encoding a human tissue plasminogen activator as set forth in any one of claims 1, 2, 3, or 4.

9. A recombinant vector encoding a human tissue plasminogen activator as set forth in any one of claims 1, 2, 3, or 4.

10. A host cell expressing a human tissue plasminogen activator as set forth in any one of claims 1, 2, 3, or 4.

11. A process for producing a human tissue plasminogen activator comprising:

providing a host cell capable of expressing a human tissue plasminogen activator as set forth in any one of claims 1, 2, 3, or 4;

culturing said cell under conditions wherein said human tissue plasminogen activator is produced; and recovering the human tissue plasminogen activator produced.

12. A pharmaceutical composition comprising a human tissue plasminogen activator according to any one of claims 1, 2, 3, or 4 in an amount sufficient to provide for dissolution of clots and a physiologically acceptable carrier.

13. The human tissue plasminogen activator of either of claim 3 or claim 4 having each of asparagine 117, asparagine 184 and asparagine 448 substituted with glutamine and having Met-525 to Pro-527 deleted.

14. A nucleic acid encoding a human tissue plasminogen activator as set forth in claim 13.

15. A pharmaceutical composition comprising a human tissue plasminogen activator according to claim 13 in an amount sufficient to provide for dissolution of clots and a physiologically acceptable carrier.

* * * * *